(12) United States Patent
Eriksson et al.

(10) Patent No.: US 9,339,405 B2
(45) Date of Patent: May 17, 2016

(54) ANKLE CONTRACTURE BOOT WITH HIGH FRICTION ANTI-ROTATION AND V-SHAPED CALF WEDGE

(71) Applicant: DEROYAL INDUSTRIES, INC., Powell, TN (US)

(72) Inventors: Thomas Eriksson, Bromma (SE); Karen Kim Turner, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 110 days.

(21) Appl. No.: 14/176,654

(22) Filed: Feb. 10, 2014

(65) Prior Publication Data

US 2015/0223961 A1    Aug. 13, 2015

(51) Int. Cl.
*A61F 5/00* (2006.01)
*A61F 5/01* (2006.01)

(52) U.S. Cl.
CPC ..................... *A61F 5/0195* (2013.01)

(58) Field of Classification Search
CPC ........... A63B 59/0014; A63B 59/0092; A63B 59/06; A63B 2059/065; A63B 2208/12; A63B 59/0029; A63B 71/141; A63B 71/143; A63B 71/0054; A63B 21/1434; A63B 59/0033; A63B 71/146; A63B 71/10; A63C 10/10; A63C 10/24; A63C 10/04; A63C 10/285; A63C 10/145; A63C 10/103; A63C 17/1418; A63C 17/067; A63C 17/226; A63C 17/1472; A63C 2017/149; A63C 2203/42; A63C 10/18; C08L 2666/02; C08L 2666/24; C08L 53/02; C08L 53/025; C08L 51/00; C08L 53/00; C08L 2666/04; C08L 23/06; C08L 23/30; C09J 53/02; C09J 153/025; C08K 5/0016; A01K 85/00; A61C 15/00
USPC ..................... 602/16, 23–28, 60–62; 128/882
See application file for complete search history.

(56) References Cited

U.S. PATENT DOCUMENTS

| 3,552,044 | A | | 1/1971 | Wiele | |
|---|---|---|---|---|---|
| 5,226,245 | A | * | 7/1993 | Lamont | 36/9 R |
| D338,067 | S | | 8/1993 | Luber et al. | |
| D351,912 | S | | 10/1994 | Turtzo et al. | |
| 5,372,576 | A | * | 12/1994 | Hicks | 602/27 |
| D375,164 | S | | 10/1996 | Wasserman et al. | |
| 6,056,712 | A | * | 5/2000 | Grim | 602/27 |
| D435,294 | S | | 12/2000 | Pior et al. | |
| 6,428,493 | B1 | | 8/2002 | Pior et al. | |
| 6,432,073 | B2 | | 8/2002 | Pior et al. | |
| 2001/0031936 | A1 | * | 10/2001 | Pior et al. | 602/27 |
| 2010/0022931 | A1 | * | 1/2010 | Varn et al. | 602/28 |

OTHER PUBLICATIONS

PCT Notification of Transmittal of the International Search Report and the Written Opinion of the International Searching Authority (PCT Rule 44.1) PCT/US14/72636 date of mailing Mar. 25, 2015.

* cited by examiner

*Primary Examiner* — Michael Brown
(74) *Attorney, Agent, or Firm* — Luedeka Neely Group, PC

(57) ABSTRACT

An ankle contracture boot having an L-shaped splint having an adjustably positionable abduction bar, and a soft boot that attaches to the splint. The ankle contracture boot includes structure for facilitating desired static positioning of the boot, structure for statically positioning the lower leg relative to the boot, and structure for reducing heel pressure.

8 Claims, 12 Drawing Sheets

ANKLE CONTRACTURE BOOT WITH HIGH FRICTION ANTI-ROTATION AND V-SHAPED CALF WEDGE

FIELD

This disclosure relates to the field of ankle contracture boots. More particularly, the disclosure relates to an ankle contracture boot having improved structure for stabilizing rotation of the leg and reducing pressure to the Achilles and the heel area.

BACKGROUND

Ankle contracture boots are soft, static ankle orthosis worn on the ankle and lower leg for patients typically confined to bed and recovering from a lower leg injury or surgical procedure. The boots are used for statically positioning the lower leg and reducing pressure, particularly on the heel, so as to reduce pressures associated with the development of heel ulcers that can arise from extended bed rest.

The present disclosure relates to improved structures for ankle contracture boots. The improved structures include structure for facilitating desired static positioning of the boot, structure for statically positioning the lower leg relative to the boot, and structure for reducing heel pressure.

SUMMARY

The disclosure relates to structures for statically positioning the lower leg and reducing pressure, particularly on the heel, so as to reduce pressures associated with the development of heel ulcers that can arise from extended bed rest.

In one aspect, the disclosure relates to an ankle support for application to a foot, ankle, and lower leg of a patient confined to a bed. The support includes a generally L-shaped splint having a leg portion and a foot portion; and an abduction bar adjustably positionable on the splint so as to be positionable to bear against the bed to inhibit rolling of the splint relative to the bed. The abduction bar includes a high friction surface operably associated with the abduction bar for contacting a surface of the bed to enhance frictional resistance and enhance stabilization of the ankle contracture boot relative to the bed.

In another aspect, the disclosure relates to an ankle contracture boot. The ankle contracture boot includes a generally L-shaped splint having a leg portion and a foot portion; a soft boot attached to the splint to secure the foot, ankle, and lower leg of the patient adjacent the splint, the soft boot including a foot portion and a leg portion; and a pressure reduction and stabilization pad located associated with the leg portion of the soft boot.

The pressure reduction and stabilization pad is configured and positioned relative to the leg portion of the soft boot to support the lower leg of the patient against rotation relative to the splint and to elevate and reduce pressure to a heel of the patient on the bed. The pressure reduction and stabilization pad includes a flexible body configured to receive the leg portion of the patient, the pressure reduction and stabilization pad including a lowermost end having an open notch configured to off-load pressure to the Achilles area and receive the heel of the patient so as to provide an anchor point for the heel within the soft boot to anchor the leg of the patient against rotation relative to the soft boot, and to elevate and reduce pressure to the heel of the patient.

In another aspect, the disclosure relates to an ankle contracture boot having a generally L-shaped splint having a leg portion and a foot portion; an abduction bar adjustably positionable on the splint so as to be positionable to bear against the bed to inhibit rolling of the splint relative to the bed; a soft boot attached to the splint to secure the foot, ankle, and lower leg of the patient adjacent the splint, the soft boot including a foot portion and a leg portion; and a pressure reduction and stabilization pad located associated with the leg portion of the soft boot.

The abduction bar includes a high friction surface operably associated with the abduction bar for contacting a surface of the bed to enhance frictional resistance and enhance stabilization of the ankle contracture boot relative to the bed.

The pressure reduction and stabilization pad is configured and positioned relative to the leg portion of the soft boot to support the lower leg of the patient against rotation relative to the splint and to elevate and reduce pressure to a heel of the patient on the bed. The pressure reduction and stabilization pad includes a flexible body configured to receive the leg portion of the patient, the pressure reduction and stabilization pad including a lowermost end having an open notch configured to off-load pressure to the Achilles area and to receive the heel of the patient so as to provide an anchor point for the heel within the soft boot to anchor the leg of the patient against rotation relative to the soft boot, and to elevate and reduce pressure to the heel of the patient.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
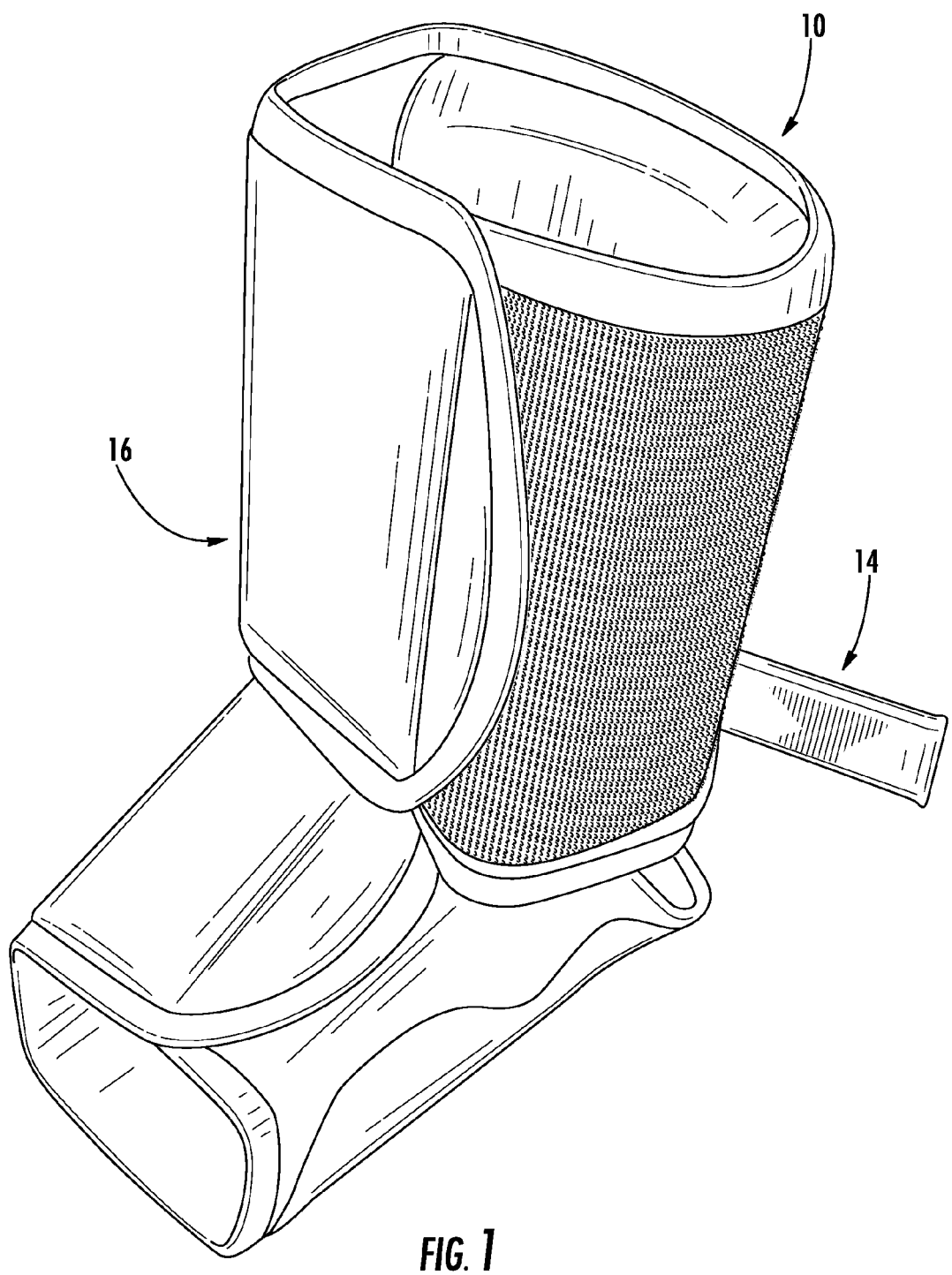
FIG. 1 is a perspective view showing an ankle contracture boot according to the disclosure.
Figure 2:
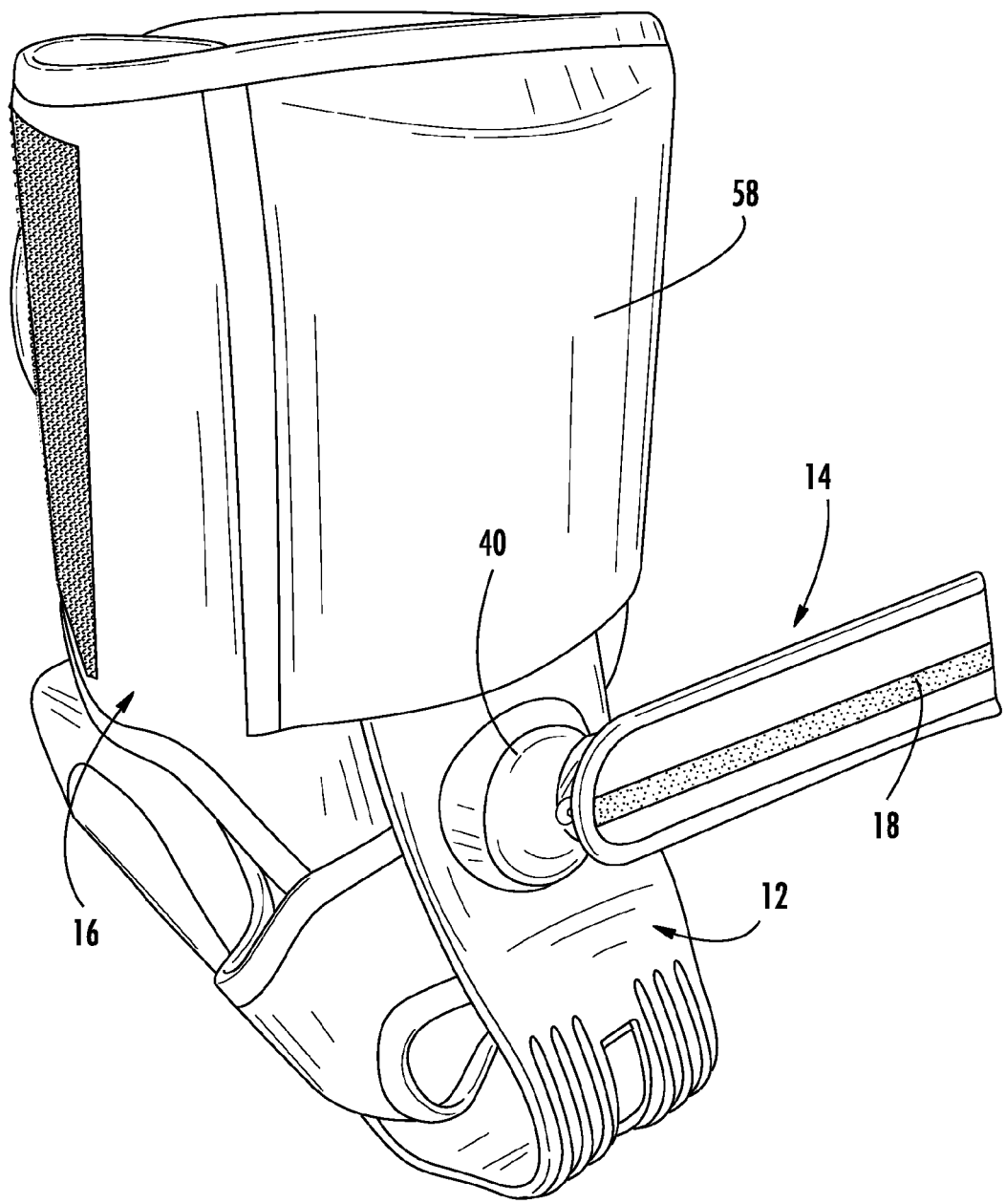
FIG. 2 is a rear view of the boot of FIG. 1.
Figure 3:
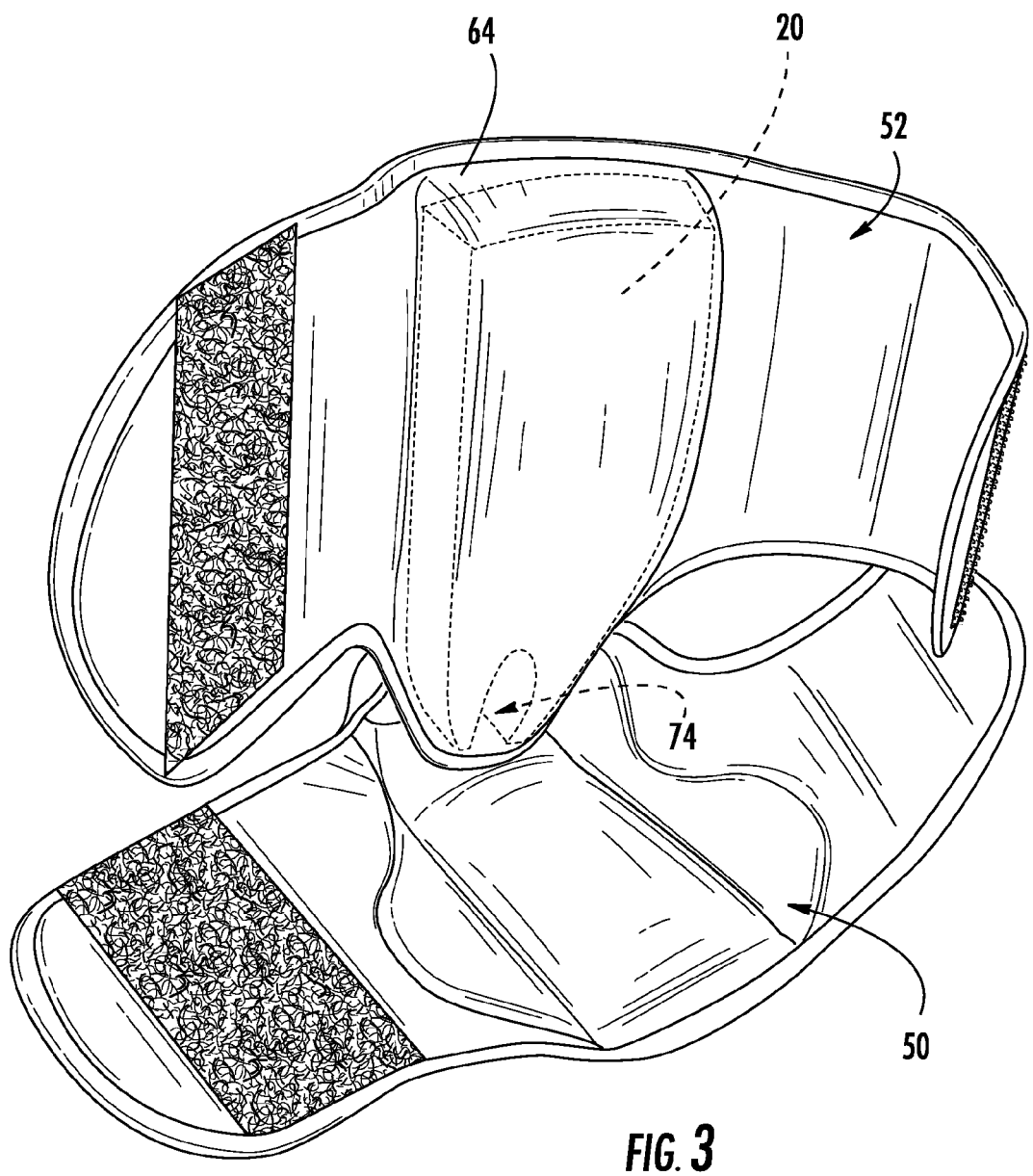
FIG. 3 shows interior portions of the boot of FIG. 1.
Figure 4:
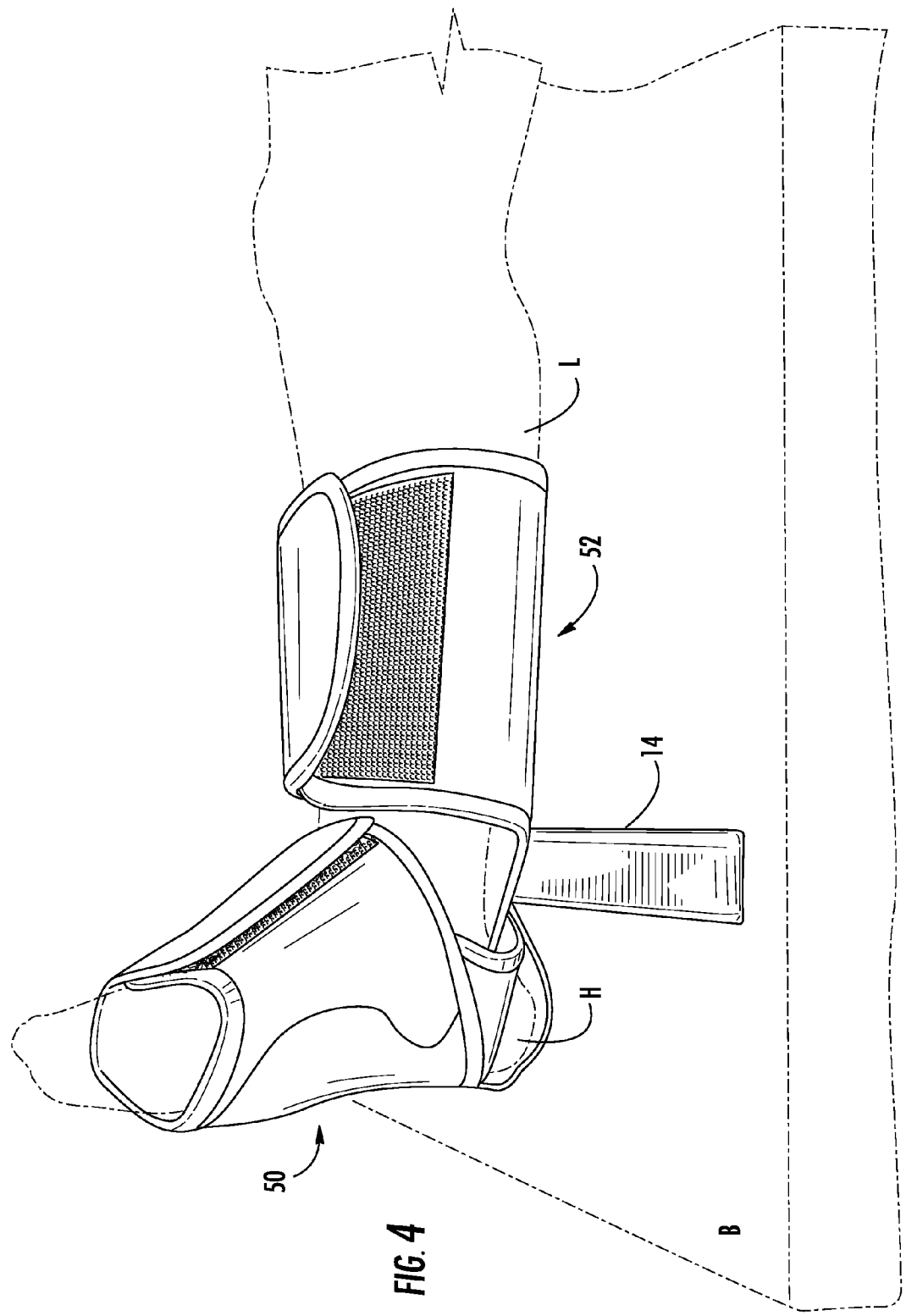
FIG. 4 depicts use of the boot of FIG. 1 to stabilize a lower leg and reduce heel pressure.

With reference to the drawings, the disclosure relates to an ankle contracture boot 10 having an L-shaped splint 12 having an adjustably positionable abduction bar 14, and a soft boot 16 that attaches to the splint 12. The boot 10 includes structure for facilitating desired static positioning of the boot, structure for statically positioning the lower leg relative to the boot, and structure for reducing heel pressure.

Significant features of the boot 10 relate to the provision of a high friction material 18 and a pressure reduction and stabilization pad 20. The high friction material 18 cooperates with the abduction bar 14 and is configured and positioned to advantageously enhance stabilization of the boot 10 relative to an underlying bed B on which a patient wearing the boot 10 is supported. This serves to advantageously inhibit rotation of the leg, including the hip, knee, and ankle of the patient. The pressure reduction and stabilization pad 20 cooperates with the soft boot 16 and is configured and positioned to advantageously support a lower leg L of the patient against rotation relative to the splint 12 and to elevate and reduce pressure to a heel H of the patient.

The splint 12 is preferably of one-piece molded plastic construction and generally L-shaped in configuration. Preferred plastic materials are substantially rigid yet enable some flexure for patient comfort, particularly during ambulation. Preferred plastic materials include ABS plastic and polypropylene. The splint 12 is preferably of substantially uniform thickness, ranging from about ⅛ to about ¼ inches, most preferably about 3/16 inches.

To provide the desired rigidity/flexure characteristics, the splint 12 preferably includes a foot portion 22 and a leg portion 24 oriented generally perpendicular to one another and connected by a bend 26. The foot portion 22 and the leg portion 24 are substantially rigid across their length and width, with the bend 26 configured to enable the portions 22 and 24 to be flexed toward and away from one another. The bend 26 may include an elongate aperture 28 centrally located thereon to enhance flexibility and a plurality of raised ribs 30 integrally molded on exterior surfaces of the splint (relative to the patient's foot and leg) on opposite sides of the aperture 28 to reinforce the bend against breakage. The aperture 28 also provides a path to enable air to flow to the patient's foot. The foot portion 22 has a foot contact surface that, while substantially flat, includes a small degree of convexity to conform generally to the arch of the patient's foot. Likewise, the leg portion 24 includes a leg contact surface that is somewhat concave to conform to the relatively semi-circular topography of the back of the patient's lower leg, mainly the calf muscle. A mounting bolt 32 or the like may be located on the bottom of the splint 12 for connecting a sole member or a toe support or other accessories to the splint 12.

It has been experienced that patients tend to relax their leg muscles, particularly when sleeping, and roll their legs so that the side of their foot contacts the bed. To inhibit this, the abduction bar 14 is rotatably mounted to the splint 12 by a mount 40 that enables the abduction bar 14 to be rotatably positioned in a plurality of orientations, and in particular in orientations substantially perpendicular to the patient's leg to inhibit the foot from rolling toward the bed.

Figure 7A:
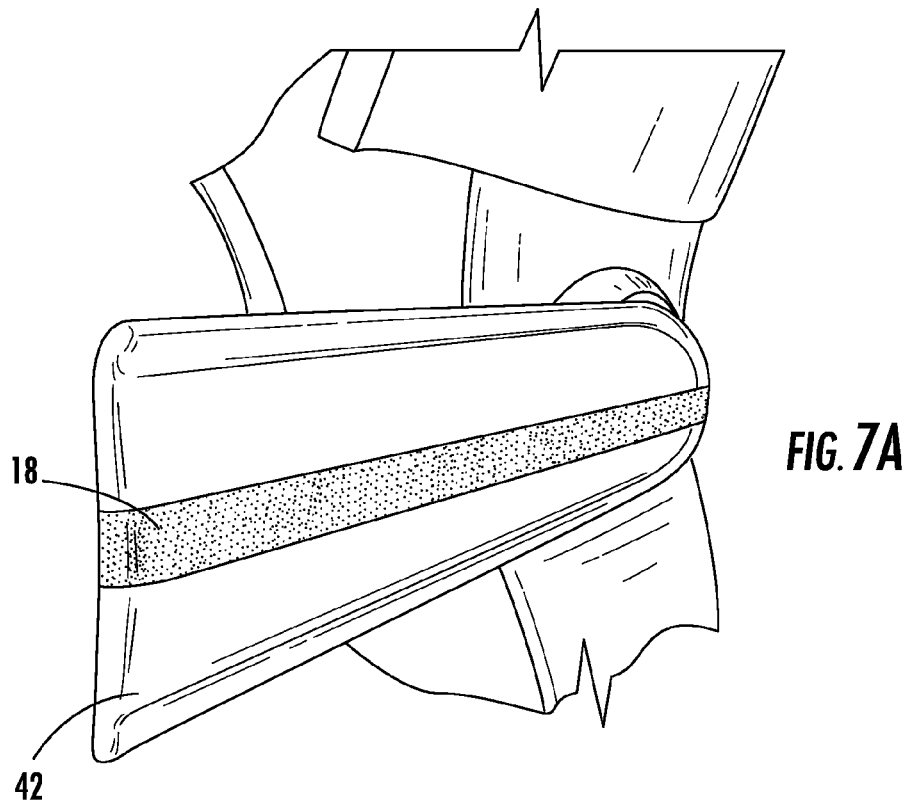
FIG. 7A is a close-up view of a cover for an abduction bar of the boot of FIG. 1.
Figure 7B:
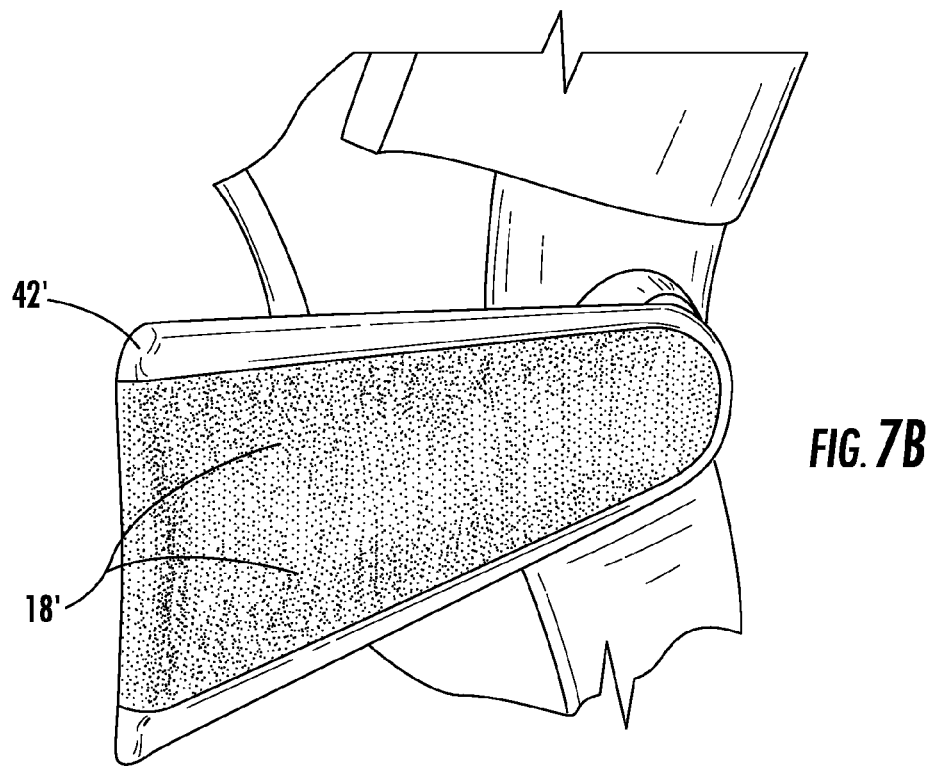
FIG. 7B is a close-up view of an alternative cover for an abduction bar of the boot of FIG. 1.
Figure 8:
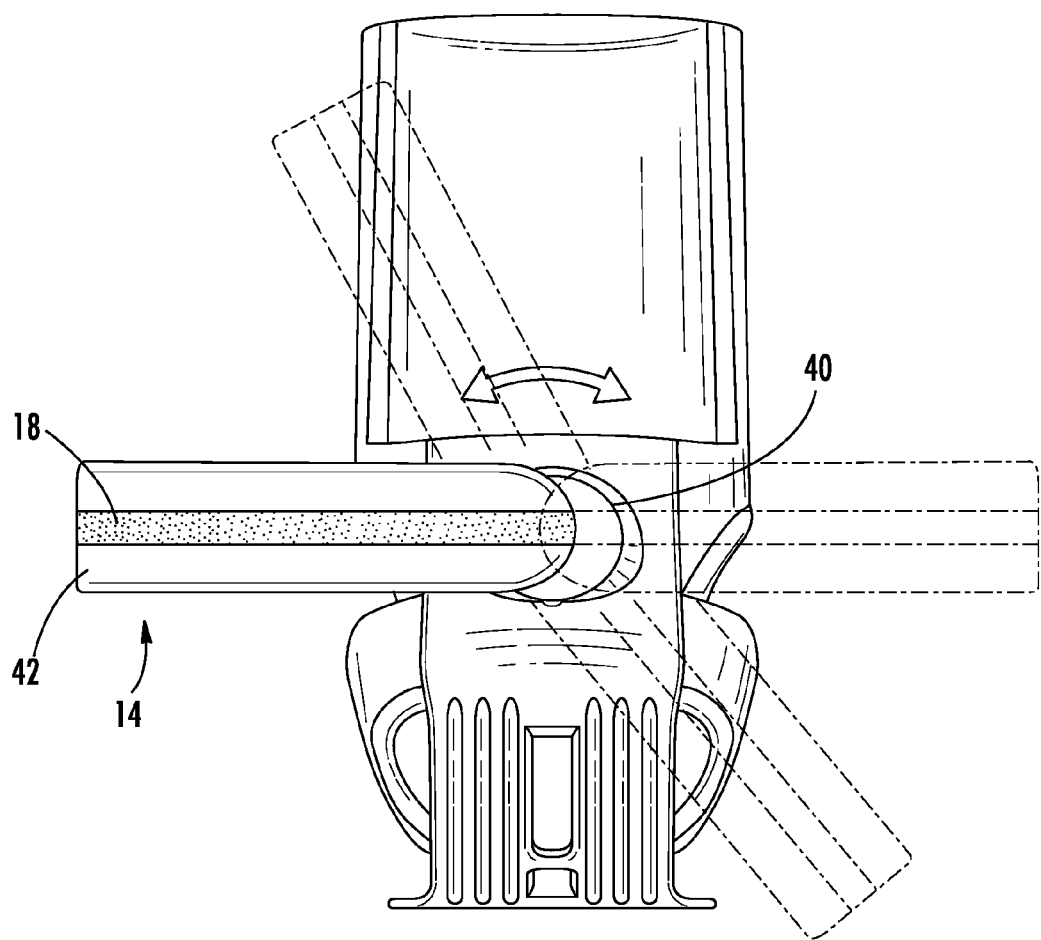
FIG. 8 depicts adjustable positioning of the abduction bar of the boot of FIG. 1.
Figure 9:
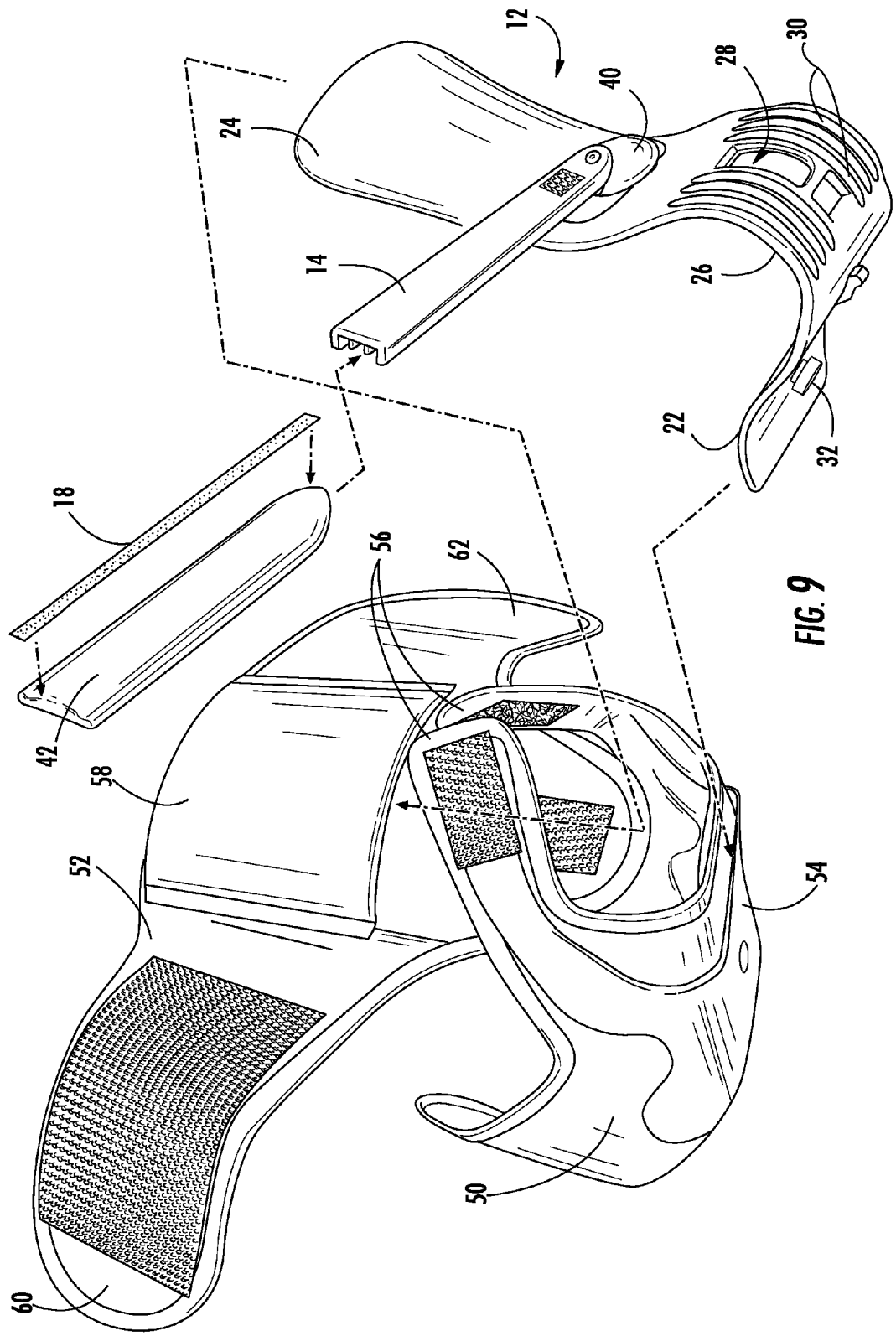
FIG. 9 is an exploded perspective view of the boot of FIG. 1
Figure 10:
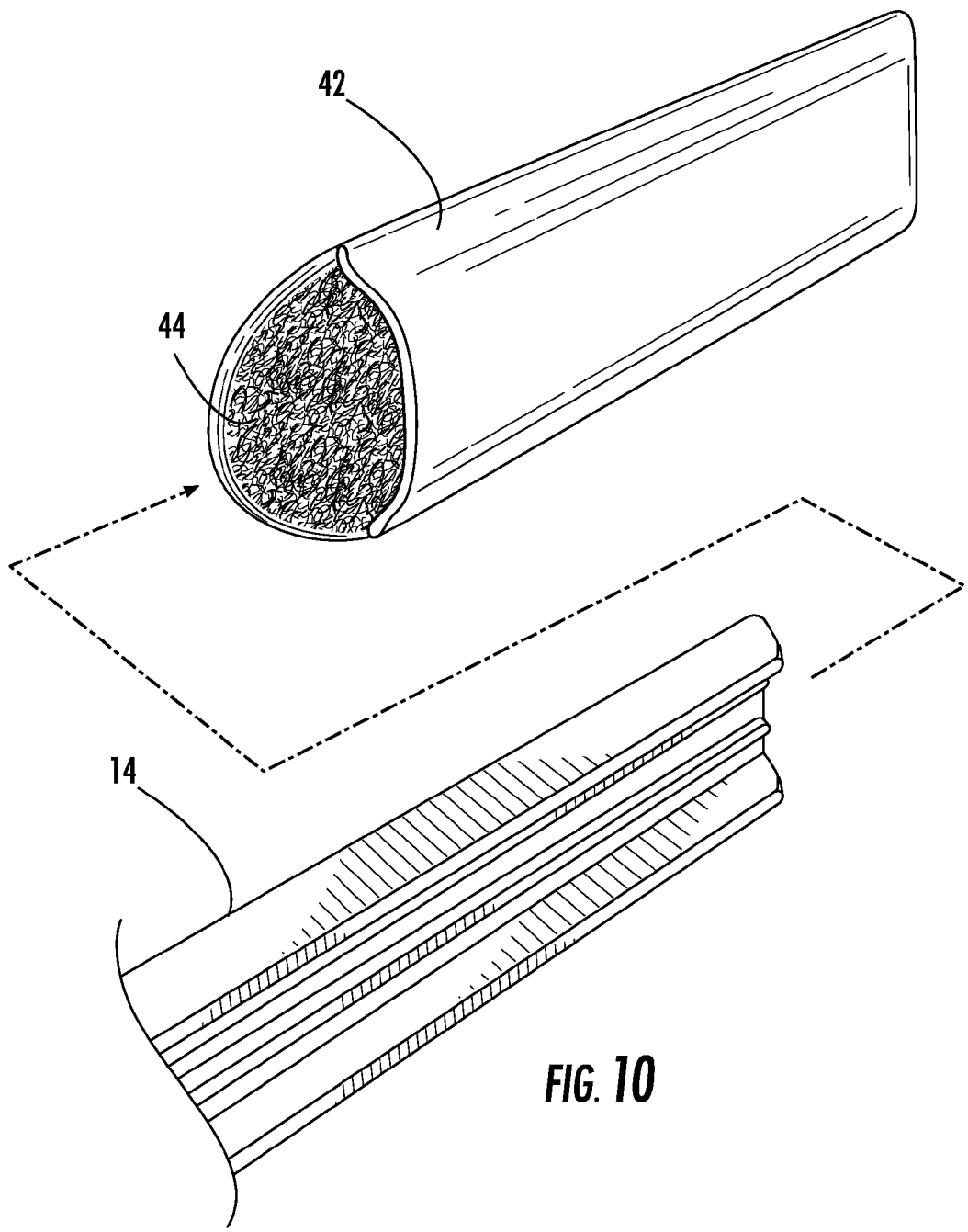
FIG. 10 is an exploded close-up view of the cover of FIG. 7A and the abduction bar onto which it is installed.

The abduction bar 14 may be made of plastic in the manner of the splint 12 and is configured as a rectangular extension of the mount 40 with a length of from about 4 to about 8 inches, most preferably about 6 inches, and a width of from about ½ to about 1½ inches, most preferably about 1 inch. The high friction material 18 may be provided by a soft silicone strip having a static coefficient of friction of at least about 0.75 or higher. Other suitable materials include raw neoprene and soft polyurethanes having relatively high static coefficients of friction, preferably of at least about 0.75 or higher. The high friction material 18 may be applied directly to the abduction bar 14, as by adhesive, or otherwise configured to cooperate with the abduction bar 14 so as to advantageously enhance stabilization of the boot 10 relative to the underlying bed B on which a patient wearing the boot 10 is supported. For example, with reference to FIG. 7A, the high friction material 18 may also be secured, as by adhesive or stitches, to a fabric cover 42 configured to be slipped over and frictionally retained on the abduction bar 14, such as having a fleece-lined interior cavity 44 (FIG. 10). Alternatively, with reference to FIG. 7B, a cover 42' may have the exterior thereof substantially covered with a high friction material 18', such as a soft silicone or other tacky material.

The soft boot 16 is configured to fit around the patient's foot, ankle and lower leg, and attaches to the splint 12 to secure the foot, ankle and leg of the patient adjacent to the splint 12. The soft boot 16 is preferably made of a soft fabric material such as fleece or vel-foam material. The boot 16 includes a foot portion 50 and a leg portion 52 that are preferably attached to one another.

The foot portion 50 of the soft boot 16 includes a substantially rectangular main body portion including an exterior pocket 54 for positioning over the foot contacting portion of the splint 12. A pair of straps 56 extend substantially perpendicularly away from the pocket for positioning around the splint 12. The straps 56 include hook/loop material at their distal ends for releasably securing the ends of the straps 56 together about the splint 12. Ends of the main body portion include matingly engagable hook/loop material for releasable securement of the foot portion about the foot of the user.

The leg portion 52 of the soft boot 16 includes a main body portion having a rear exterior pocket 58 for receiving the leg portion of the splint 12. Opposite ends 60 and 62 of the main body portion of the soft boot 16 are configured to wrap around the leg of the user and overlap, with the ends thereof having cooperating hook/loop material.

The pressure reduction and stabilization pad 20 is located within a pocket or compartment 64 of the leg portion 52 of the soft boot 16. The compartment 64 is located to position the pad 20 to overlie the leg portion 24 of the splint 12 so that the pad 20 is between the leg L of the user and the leg portion 24 of the splint 12 during use of the boot 10.

Figure 5:
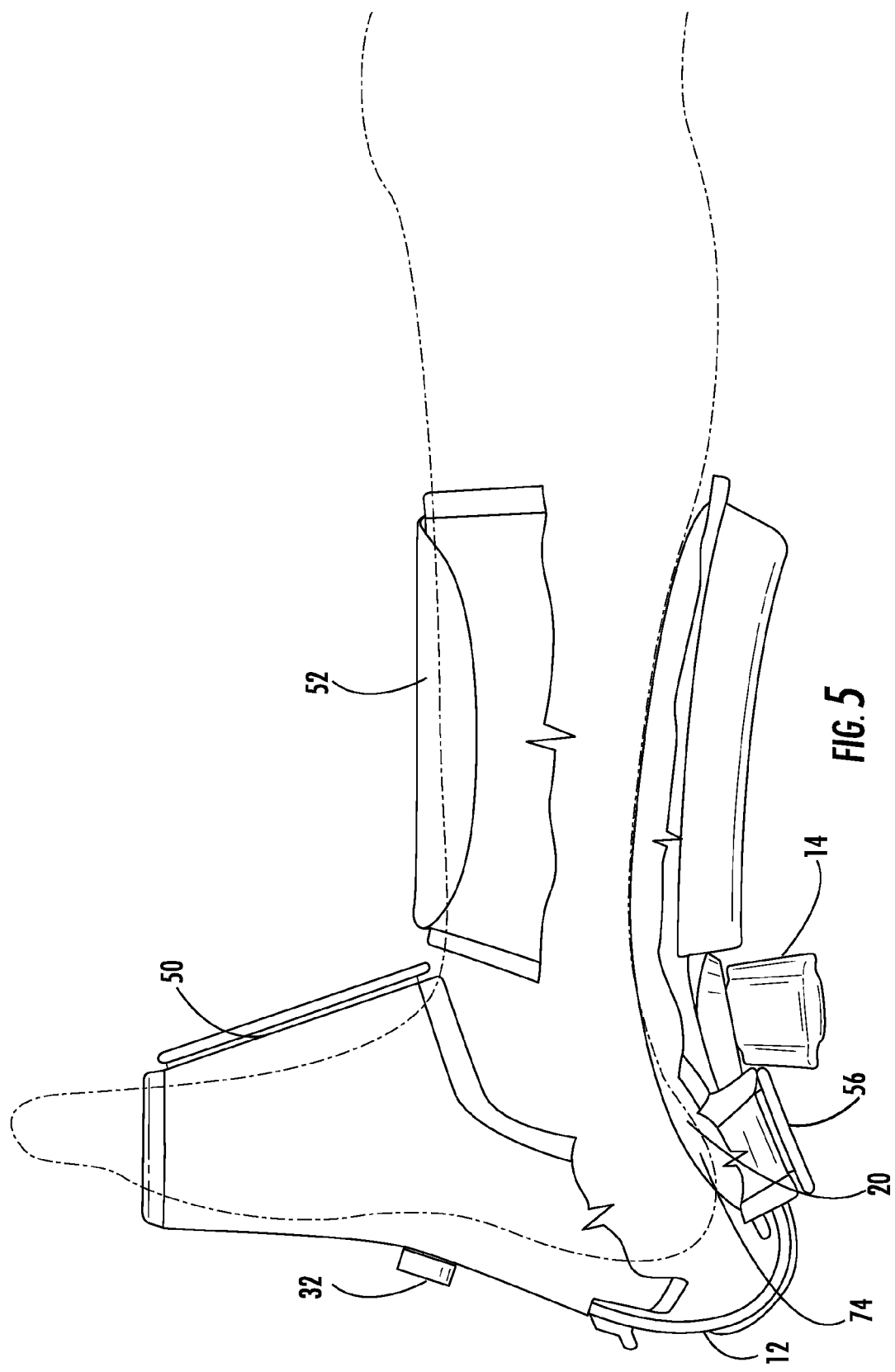
FIG. 5 shows use of the boot as in FIG. 4, with portions of the boot cut-away.
Figure 6:
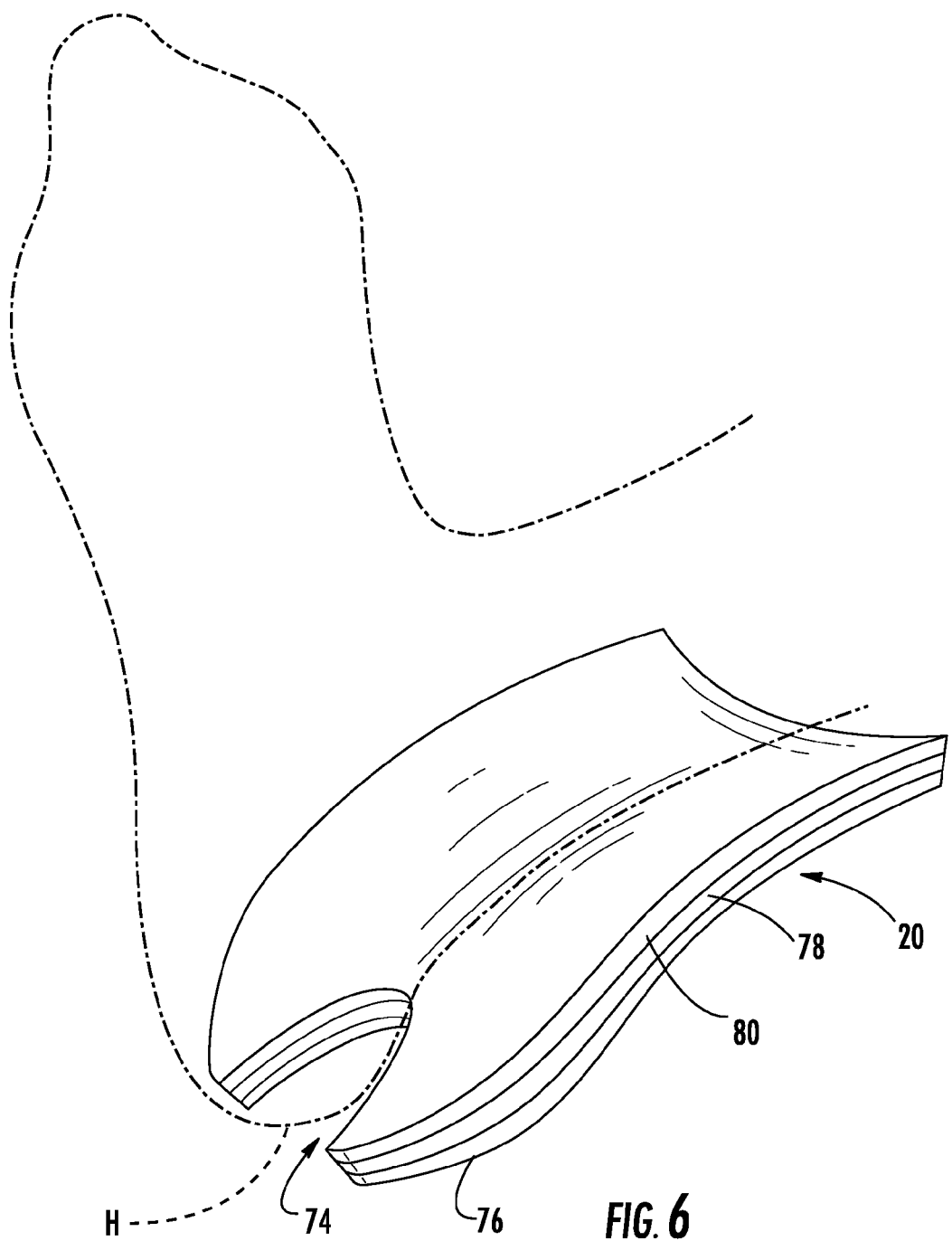
FIG. 6 shows a pressure reduction and stabilization pad cooperating with the lower leg and heel during use of the boot of FIG. 1.
Figure 11:
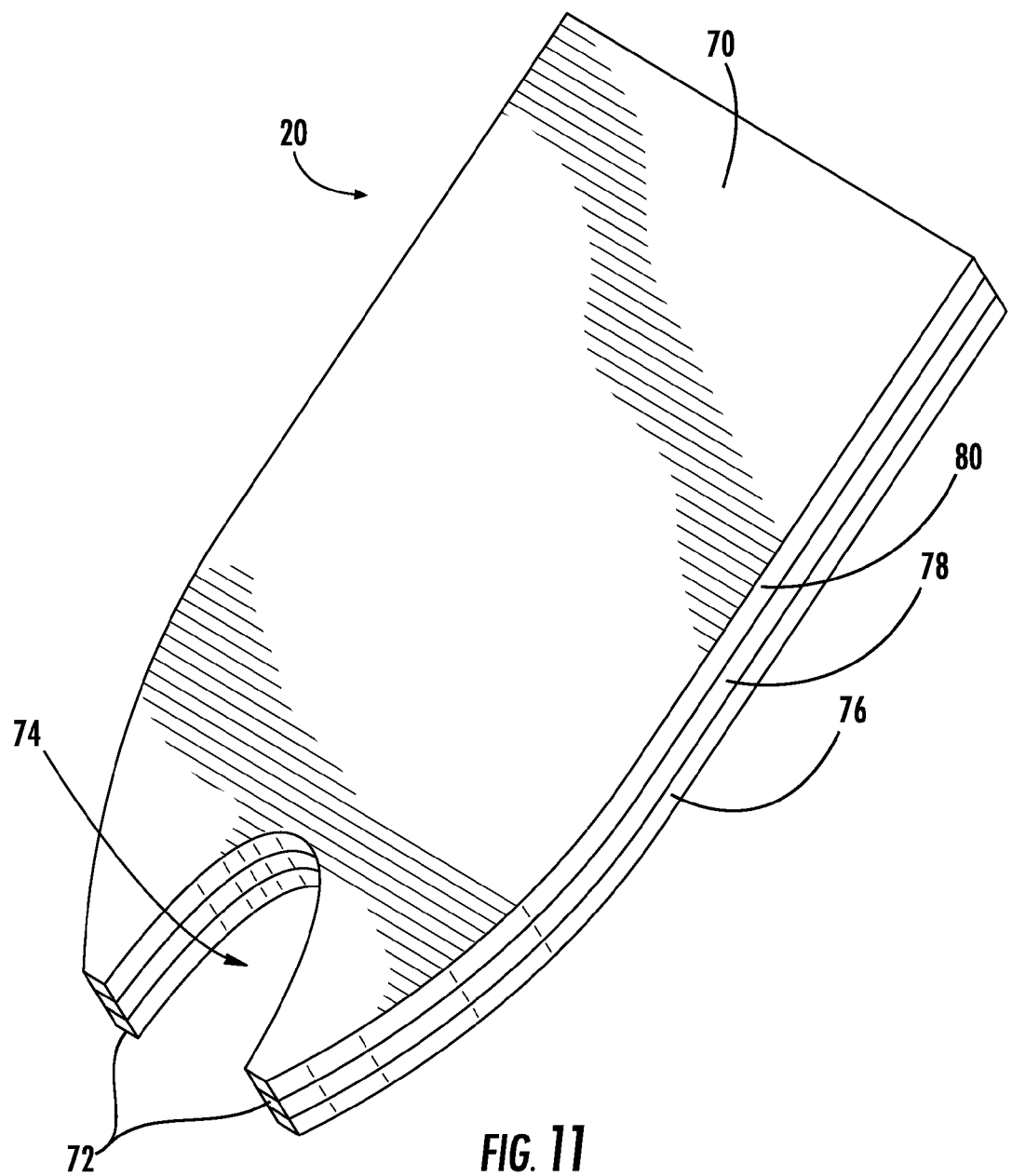
FIG. 11 is a perspective view of a pressure reduction and stabilization pad of the boot of FIG. 1.
Figure 12:
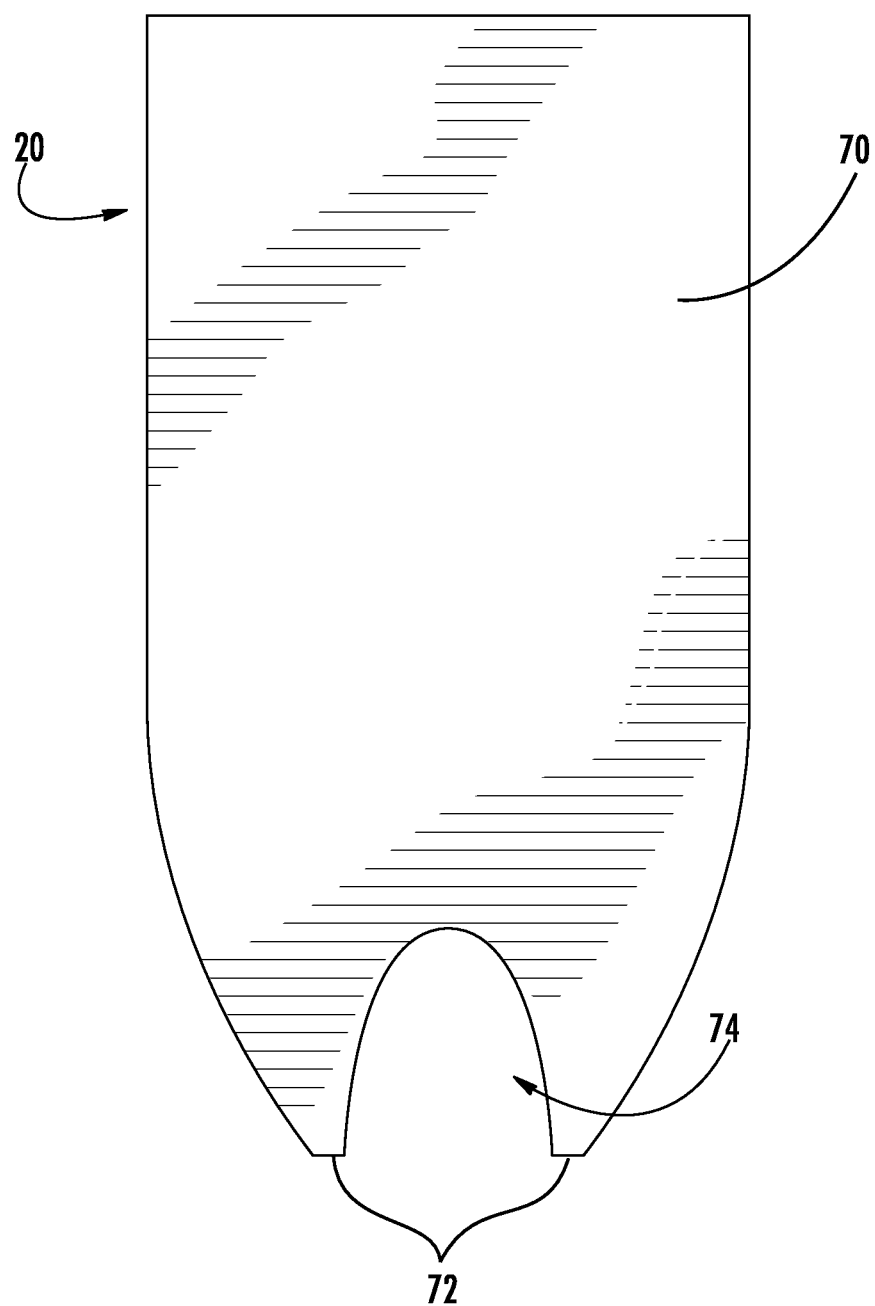
FIG. 12 is a plan view of the pad of FIG. 11.

With additional reference to FIGS. 11 and 12, the pad 20 is configured to have a substantially rectangular body 70, with a lowermost tapered end 72 configured to include a generally U-shaped or V-shaped notch 74. The notch 74 is configured to receive the heel H of the patient (FIGS. 5 and 6) so as to provide an anchor point for the heel H within the soft boot 16 that anchors the leg L of the user against rotation relative to the soft boot 12, and hence the against rotation relative to the boot 10. The configuration of the pad 20 having the notch 74 as located in the boot 10 also advantageously elevates and reduce pressure to the heel H of the patient.

The pad 20 is desirably flexible so as to conform to the curvature of the splint 12 and to cradle the leg L of the user. The pad 20 may be made to have a bottom layer 76 that is made of a dense or low compressibility foam material, with overlying less dense layers 78 and 80 each made of a viscoelastic foam material. It has been observed that this three-layer structure is advantageous to enable the pad 20 to maintain an arched orientation in the boot 10 and inhibit the pad 20 from bottoming out, in addition to protecting the calf of the leg L from possible pressure from the splint 12. Other suitable pad materials for forming the pad 20 include materials suitable for supportably contacting the leg L for long term bed rest, such as conformable gel pads, gas and liquid filled pads, and pads filled with elastomeric materials, and the like.

During use of the boot 10, the abduction bar 14 as augmented by the incorporation of a high friction material, such as the high friction materials 18 and 18', serves to offer enhanced anti-rotation of the boot 10 as compared to conventional boots not having any structure corresponding to the high friction materials 18 or 18'. Furthermore, additional improvements are achieved by incorporation of the pad 20 into the boot structure. For example, the pad 20 as located in the boot 10 and configured to include the notch 74, serves to capture the heel H of the patient to inhibit rotation of the heel h and the leg 1 of the patient relative to the boot 10. Also, the structure of the pad 20 with the notch 74, as incorporated into the boot 10 serves to elevate and reduce pressure to the heel H of the patient during bed rest.

Accordingly, it will be appreciated that structures according to the disclosure facilitate desired static positioning of the boot and the lower leg of the patient, while also reducing heel pressure.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. An ankle contracture boot for application to a foot, ankle, and lower leg of a patient confined to a bed, the ankle contracture boot comprising:
    a generally L-shaped splint having a leg portion and a foot portion;
    a soft boot attached to the splint to secure the foot, ankle, and lower kg of the patient adjacent the splint, the soft boot including a foot portion and a leg portion; and
    a pressure reduction and stabilization pad located associated with the leg portion of the soft boot, the pressure reduction and stabilization pad being configured and positioned relative to the leg portion of the soft boot to support the lower leg of the patient against rotation relative to the splint and to elevate and reduce pressure to a heel of the patient on the bed, the pressure reduction and stabilization pad comprising a flexible body configured to receive the leg portion of the patient, the pressure reduction and stabilization pad including a lowermost end having an open notch configured to off-load pressure to the Achilles area and to receive the heel of the patient so as to provide an anchor point for the heel within the soft boot to anchor the leg of the patient against rotation relative to the soft boot, and to elevate and reduce pressure to the heel of the patient.

2. The ankle contracture boot of claim 1, wherein the pressure reduction and stabilization pad is located within a compartment of the leg portion of the soft boot.

3. The ankle contracture boot of claim 1, wherein the open notch is substantially U-shaped or V-shaped.

4. The ankle contracture boot of claim 1, wherein the pressure reduction and stabilization pad has a bottom layer made of a low compressibility material, with a pair of overlying layers each made of a viscoelastic foam material.

5. An ankle contracture boot for application to a foot, ankle, and lower leg of a patient confined to a bed, the ankle contracture boot comprising:
    a generally L-shaped splint having a leg portion and a foot portion;
    an abduction bar adjustably positionable on the splint so as to be positionable to bear against the bed to inhibit rolling of the splint relative to the bed, the abduction bar including a high friction surface operably associated with the abduction bar for contacting a surface of the bed to enhance frictional resistance and enhance stabilization of the ankle contracture boot relative to the bed;
    a soft boot attached to the splint to secure the foot, ankle, and lower leg of the patient adjacent the splint, the soft boot including a foot portion and a leg portion; and
    a pressure reduction and stabilization pad located associated with the leg portion of the soft boot, the pressure reduction and stabilization pad being configured and positioned relative to the leg portion of the soft boot to support the lower leg of the patient against rotation relative to the splint and to elevate and reduce pressure to a heel of the patient on the bed, the pressure reduction and stabilization pad comprising a flexible body configured to receive the leg portion of the patient, the pressure reduction and stabilization pad including a lowermost end having an open notch configured to receive the heel of the patient so as to provide an anchor point for the heel within the soft boot to anchor the leg of the patient against rotation relative to the soft boot, and to elevate and reduce pressure to the heel of the patient.

6. The ankle contracture boot of claim 5, wherein the high friction material comprises silicone.

7. An ankle support for application to a foot, ankle, and lower leg of a patient confined to a bed, the ankle support comprising:
    a generally L-shaped splint having a leg portion and a foot portion; and
    an abduction bar adjustably positionable on the splint so as to be positionable to bear against the bed to inhibit rolling of the splint relative to the bed, the abduction bar including a high friction surface having a static coefficient of friction of at least about 0.75 operably associated with the abduction bar for contacting a surface of the bed to enhance frictional resistance and enhance stabilization of the ankle contracture boot relative to the bed to inhibit rotation of the leg of the patient.

8. The ankle support of claim 7, wherein the high friction material comprises silicone.

\* \* \* \* \*